United States Patent [19]

Gottlieb

[11] Patent Number: 4,874,608
[45] Date of Patent: * Oct. 17, 1989

[54] THERAPEUTIC METHOD FOR TREATING MALIGNANCIES

[75] Inventor: A. Arthur Gottlieb, New Orleans, La.

[73] Assignee: Imreg, Inc., New Orleans, La.

[*] Notice: The portion of the term of this patent subsequent to Aug. 28, 2001 has been disclaimed.

[21] Appl. No.: 43,175

[22] Filed: Apr. 27, 1987

[51] Int. Cl.$^4$ .................. A61K 37/02; A61K 35/00
[52] U.S. Cl. ................................ 424/85.1; 514/18; 514/19; 514/21
[58] Field of Search ...................... 514/18, 19, 21; 424/85.1

[56] References Cited

U.S. PATENT DOCUMENTS

| | | | |
|---|---|---|---|
| 4,132,776 | 1/1979 | Jeter | 424/101 |
| 4,401,658 | 8/1983 | Bouchaudon et al. | 514/18 |
| 4,457,867 | 7/1984 | Ishida | 530/351 |
| 4,468,379 | 8/1984 | Gottlieb | 424/88 |
| 4,619,915 | 10/1986 | Ives | 514/18 |
| 4,699,898 | 10/1987 | Gottlieb | 514/18 |
| 4,710,380 | 12/1987 | Gottlieb | 514/19 |
| 4,716,151 | 12/1987 | Jolles et al. | 514/18 |

Primary Examiner—Delbert R. Phillips
Assistant Examiner—Christina Chan
Attorney, Agent, or Firm—Richard H. Stern

[57] ABSTRACT

A method is described for treating mammalian solid tumors by administering leukocyte-derived amplifiers of the immune system to tumor-bearing subjects. The amplifiers include Beta-1.0, Beta-1.1, Beta-1,12, TG, and TGG.

11 Claims, No Drawings

THERAPEUTIC METHOD FOR TREATING MALIGNANCIES

BACKGROUND

It is believed that the mammalian immune system plays a significant role in preventing and retarding malignancies. More specifically, it is believed that a subset of lymphocytes known as natural killer (NK) cells scavenge cancer cells from the body, thereby preventing or retarding their proliferation.

It has been observed that pathological conditions characterized by reduced immune system response may also be accompanied by reduced NK cell activity. Further, such conditions may be accompanied by increased tendency toward the development of malignancies. For example, Kaposi's sarcoma has a greatly increased incidence among person suffering from impaired immune systems, as in acquired immune deficiency syndrome (AIDS) and AIDS-related complex (ARC). Researchers have observed decreased NK activity in some of these patients, along with other indicia of decreased immune system response.

The inventor has described in U.S. Pat. Nos. 4,468,379 and 4,616,079, and in various pending patent applications (Ser. No. 813,632, now U.S. Pat. No. 4,699,898, and 902,683, now abandoned) the discovery of biological materials termed "immunomodulators" or "modulators of the immune system," which are capable of modulating the speed and/or intensity of immune system response. A subset of these immunomodulators are "immunoamplifiers" or "amplifiers," which are capable of increasing the speed and/or intensity of immune system response. As explained in the cited patent and patent applications, these materials are distinguished from previously described "transfer factors," which are materials said to have the capability of transferring from a donor to a donee an immune response to a specific antigen, even though the donee has not previously been exposed to that particular antigen. In contrast, amplifiers are not specific to particular antigens and operate more generally (non-specifically). Further, amplifiers increase immune system response only to antigens to which the donee has previously been or is concurrently exposed, and they do not transfer an immune system response to an antigen to which the donee has yet to be exposed.

As described in the cited patent and patent applications, amplifiers may be extracted from human lymphocyte samples, and are relatively low M.W. materials that are elutable by HPLC using various solvent and gradient systems. Analytic tests suggest that active ingredients of the "Beta" amplifier are the dipeptide TG and the tripeptide TGG and/or their derivatives (see '683 patent application). The inventor has discovered that, when appropriately purified, commercially available TG and TGG chemical can produce substantial amplifier effects. The inventor hypothesizes that mammalian immune systems have evolved derivatives of the enkephalins as a material for modulating immune system response and for maintaining its homeostasis.

The '683 patent application also describes purification of Beta-1.0 material into components designated Beta-1.11 and Beta-1.12, amino acid residue analysis of said components as TG and TGG, and methods of modifying the TG and TGG molecules to provide derivatives that are more highly resistant to hydrolysis or enzymatic degradation.

SUMMARY OF INVENTION

The inventor has discovered that administration of amplifiers of the "Beta" type both increases NK activity and improves survival in malignancies. Observations have been made with respect to animal subjects and a human subject. Administration of appropriate dosages of amplifier has been observed to improve longevity of subjects and to improve the physical condition of a human subject. It is hypothesized that the administration of amplifier to a subject stimulates the subject's NK activity, and that this in turn leads to removal of malignant cells from the subject's body, thereby retarding or preventing the proliferation of malignant cells.

DETAILED DESCRIPTION

Animal tests

Animal tests were carried out with a strain of white mice known as Balb/c, which are available from Jackson Laboratories (Bar Harbor, Me., U.S.A.). These mice develop myeloma when injected with a preparation (described below as Preparation C) of 25,000 MOPC-21 tumor cells taken from mice known to have the MOPC-21 myeloma tumor. The basic protocol was to have three groups of mice, all of which were injected with Preparation C; two groups were treated with different dosages of Beta-1.0 amplifier purified in accordance with the procedure of Example 5 of the '683 patent application, and the third group was an untreated control. It was observed that the mice injected with tumor cells and not given Beta-1.0 had the lowest rate of survival, while the other groups had substantially higher survival rates.

An effective dosage amount of amplifier for stimulation of immune response in human subjects was previously determined by clinical testing in patients with AIDS/ARC to be that amount of amplifier derived from 400,000 leukocytes. This may be scaled down to mice by use of body weight ratios.

EXAMPLE 1

Preparation C

MOPC-21 tumor was harvested from Bulb/c mice as an ascitic tumor cell suspension. Ascites fluid containing MOPC-21 tumor cells was obtained and pooled from several tumor-bearing mice. The number of tumor cells/ml was adjusted by appropriate dilution in normal saline, so that 25,000 MOPC-21 tumor cells were contained in 0.1 ml volume.

0.1 ml of cell suspension was injected subcutaneously into the axilla. Control mice received 0.1 ml of normal saline.

EXAMPLE 2

Administration of Preparation C

A group of 5 mice of the Bulb/c strain was designated Group I. Each mouse was injected with 0.1 ml of Preparation C.

A second group of 5 mice of the same strain was designated Group II and was also injected with 0.1 ml of Preparation C.

A third group of 5 mice of the same strain was designated Group III and was also injected with 0.1 ml of Preparation C.

EXAMPLE 3

Administration of Beta

Immediately after the procedure of Example 2, the mice of Group I were each given interperitoneal injections of 0.15 ml of a saline solution containing 600,000 leukocyte equivalents of Beta-1.0 purified in accordance with the procedure of Example 5 of the '683 patent application. (On a body weight basis, this is equivalent to 5 times effective human dosage amount.)

The mice in Group II received 0.15 ml of a saline solution containing 60,000 leukocyte equivalents of Beta-1.0 (On a body weight basis, this is equivalent to 0.5 times effective human dosage amount.)

The mice in Group III received 0.15 ml of sterile saline.

The foregoing injections were respectively repeated at weekly intervals for 5 weeks.

EXAMPLE 4

Assay

All of the mice developed subcutaneous, solid MOPC-21 tumors. All of the mice alive at the end of 40 days were sacrificed and examined. Those mice that died during the preceding period were examined promptly after death. The results are tabulated below.

|  | PERCENTAGE SURVIVING | | | | | | |
|---|---|---|---|---|---|---|---|
| DAY | 15 | 20 | 24 | 27 | 35 | 37 | 40 |
| GROUP I | 100 | 100 | 80 | 80 | 80 | 80 | 80 |
| GROUP II | 100 | 100 | 100 | 100 | 60 | 60 | 60 |
| GROUP III | 100 | 100 | 80 | 60 | 40 | 20 | 20 |

It is thus seen that the treatment of the mice with Beta-1.0 was associated with a lower death rate from malignancy, since the Group III mice had a substantially lower survival than the Groups I and II mice. It may be predicted that similar results will obtain when the components of Beta-1.0 having intrinsic amplifier activity, viz., TG and TGG, are used in the same procedures in place of Beta-1.0

EXAMPLE 5

TG Procedure

The procedure of Examples 1-4 is repeated. However, in Group I, a dosage of 150 pg of TG is used in place of Betz-1.0, and in Group II 15 pg of TG is used.

The same results are observed as in Example 4.

EXAMPLE 6

TGG Procedure

The procedure of Examples 1-4 is repeated. However, in Group I, a dosage of 150 pg of TGG is used in place of Beta-1.0, and in Group II 15 pg of TGG is used.

The same results are observed as in Example 4.

The foregoing tests suggest that TG and TGG treatment prolongs the lives of the mice having malignancies.

HUMAN DATA

Human data is derived from Patient N, a colleague of the inventor, who was diagnosed in January 1985 as having carcinoma of the colon, and who eventually died from the cause in early 1986. Beginning on May 8, 1985, Patient N was given a dosage, every 2 weeks, of the amount of Amplifier Beta-1.0 of the '683 patent application derived from approximately 400,000 leukocytes. This treatment continued from May 8, 1985, to his death in February 1986. Patient N also received extensive chemotherapy in the form of fluorouracil and methotrexate. This dosage has been used in AIDS-/ARC patients to improve immune system function and has been found to be an effective dosage amount for that indication.

During this period, Patient N's NK activity was determined by standard methods prior to treatment with Beta-1.0 and periodically thereafter. Before treatment, Patient N's NK activity was below normal. Eight days after his treatment with Beta-1.0 began, his NK activity had risen significantly, from approximately 30% of normal to approximately 70% of normal. His NK activity was maintained at a higher level for a period of several months. Maintenance of these high levels of NK activity was unexpected in a patient receiving extensive chemotherapy.

While Patient N's NK activity was not restored to normal levels by the treatment, his NK activity was significantly enhanced. The inventor believes the NK activity has to be restored to at least approximately 70-75% of normal to have a significant effect against proliferation of tumor cells.

NK activity was determined by targeting K562 cells from American Type Culture Collection with effector cells from the patient (a lymphocyte population with 10-15% NK content), using four different ratios of effector:target (typically, 100;1, 50:1, 25:1, and 10:1), and tabulating the resulting lysis. The data from different post-treatment assays do not differ significantly, although the data appeared to improve as treatment with Beta-1.0 continued. A representative before-after comparison (after the first week of treatment) is as follows:

|  | % LYSIS | |
|---|---|---|
| EFFECTOR-TARGET RATIO | BEFORE | AFTER |
| 100:1 | 54.3% | 69.6% |
| 50:1 | 41.7 | 58.6 |
| 25:1 | 22.1 | 51.4 |
| 10:1 | 7.9 | 31.8 |

It is the inventor's medical opinion that Patient N's life was prolonged from 3 to 6 months as a result of the treatment with amplifier Beta-1.0, and that because of his improved immune response his state of health was better in 1985 and 1986 than could otherwise have been expected in the circumstances.

The foregoing experimental data support the hypotheses that the administration of amplifier increases NK activity, that the resulting increased NK activity tend to prevent or retard the proliferation of malignant cells, and that the latter in turn is useful in treatment of malignancies. The animal and human data are consistent with the hypotheses, and there does not appear to be a more plausible alternative hypothesis to account for the data.

GENERAL CONCLUDING REMARKS

The above described procedures disclose what the inventor believes is a unique and hitherto unknown method of treating human or animal subjects for malignant disorders. While the invention has been described primarily in connection with a specific and preferred embodiment thereof, it will be understood that it is capable of further modifications without departing from the spirit and scope of the invention. This application is intended to cover all variations, uses, or adaptations of the inventions, following, in general, the principles of the invention and including such departures from the present disclosure as come within known or customary practice within the art to which the invention pertains, or as are obvious to persons skilled in the art, at the time the departure is made.

As used in the claims, the term "derivative," when applied to TG and TGG, refers to the types of molecular variations described in the '683 patent application. The term, when applied to Beta-1.0, refers to the foregoing and also to more highly purified extracts of Beta-1.0, such as Beta-1.11 and Beta-1.12, described in the same patent application.

The subject matter claimed is:

1. A method of treating mammalian solid tumors comprising administering to a mammalian subject an effective dosage amount of at least one amplifier of the immune system, where said amplifier essentially consists of at least one of the following: Beta-1.0, TG, or TGG.

2. The method of claim 1 wherein said amplifier is TG, TGG, or a mixture of TG and TGG.

3. The method of claim 1 wherein the subject is human.

4. The method of claim 3 wherein the amplifier is Beta-1.0.

5. The method of claim 3 wherein the dosage amount is sufficient to raise the subject's NK activity to within at least approximately 70 to 75% of normal human NK activity.

6. A method of treating a person for solid tumors comprising administering to the person an effective dosage amount of TG, TGG, or a mixture of TG and TGG.

7. A method of treating a person for solid tumors comprising administering to the person an effective dosage amount of an amplifer of the human immune system, where said amplifier essentially consists of Beta-1.0, TG, and TGG.

8. The method of claim 7 wherein the dosage amount is sufficient to raise the subject's NK activity to within 30 to 70% of normal human NK activity.

9. The method of claim 8 wherein the tumor is colon cancer.

10. The method of claim 2 wherein the tumor is myeloma.

11. A method of treating a person for solid tumors comprising administering to the person an effective dosage amount of at least one of the following amplifiers of the human immune system: Beta-1.11, Beta-1.12.

* * * * *